United States Patent
Delledonne et al.

(10) Patent No.: US 7,368,622 B2
(45) Date of Patent: May 6, 2008

(54) PROCESS FOR THE PREPARATION OF 1-OCTENE

(75) Inventors: Daniele Delledonne, Oleggio-Novara (IT); Franco Rivetti, Milan (IT)

(73) Assignee: Polimeri Europa S.p.A., Brindisi (IT)

( * ) Notice: Subject to any disclaimer, the term of this patent is extended or adjusted under 35 U.S.C. 154(b) by 0 days.

(21) Appl. No.: 10/576,144

(22) PCT Filed: Oct. 11, 2004

(86) PCT No.: PCT/EP2004/011460

§ 371 (c)(1),
(2), (4) Date: Dec. 13, 2006

(87) PCT Pub. No.: WO2005/047217

PCT Pub. Date: May 26, 2005

(65) Prior Publication Data

US 2007/0129585 A1    Jun. 7, 2007

(30) Foreign Application Priority Data

Oct. 27, 2003    (IT)  .......................... MI2003A2085

(51) Int. Cl.
*C07C 2/04* (2006.01)
*C07C 5/05* (2006.01)
(52) U.S. Cl. ....................... 585/329; 585/324; 585/273
(58) Field of Classification Search ................. 585/329, 585/324, 273
See application file for complete search history.

(56) References Cited

U.S. PATENT DOCUMENTS 4,229,605 A    10/1980   Nozaki
4,243,829 A    1/1981   Pittman et al.

FOREIGN PATENT DOCUMENTS

EP   0 008 139   2/1980
EP   0 704 417   4/1996
WO   03/031378   4/2003

OTHER PUBLICATIONS

Roffia, P. et al., "Catalysis by palladium salts IV. selective hydrogenation with formic acid in the palladium catalysed dimerisation of 1,3-butadiene; syntheses of 1,7-octadiene", Journal of Organometallic Chemistry, vol. 55, pp. 405-407, 1973.
U.S. Appl. No. 10/576,463, filed Apr. 20, 2006, Delledonne.

*Primary Examiner*—Thuan Dinh Dang
(74) *Attorney, Agent, or Firm*—Oblon, Spivak, McClelland, Maier & Neustadt, P.C.

(57) ABSTRACT

Process in two steps for the preparation of 1-octene starting from butadiene which comprises: a first step (a) in which the bis-hydrodimerization of butadiene to 1,7-octadiene is effected in the presence of a catalyst based on a palladium complex containing one or more tri-substituted monodentate phosphines, in an aprotic polar solvent optionally containing an organic base; a second step (b) in which the partial catalytic hydrogenation of 1,7-octadiene to 1-octene is effected, the above process being characterized in that: (i) in the first step the aprotic polar solvent is selected from disubstituted cyclic ureas; (ii) in the second step the catalyst is selected from non supported ruthenium complexes having general formula (II): $RuX_mL_n$ (II).

17 Claims, No Drawings

PROCESS FOR THE PREPARATION OF 1-OCTENE

The present invention relates to a process for the preparation of 1-octene from butadiene in two steps, more specifically, a first step for the catalytic bis-hydrodimerization of butadiene to 1,7-octadiene in the presence of a hydrogen donor, in an aprotic polar solvent selected from disubstituted cyclic ureas, and a second step for the partial and selective reduction of 1,7-octadiene with hydrogen to 1-octene in the presence of a catalytic system comprising a non-supported ruthenium complex.

1-octene is widely applied in the field relating to the production of linear low density polyethylene (LLDPE), a copolymer obtained starting from ethylene and 1-olefins, as it imparts improved mechanical characteristics and a better weldability to the end-product. It is also applied in the field of plasticizers after hydroformylation, reduction to linear alcohols and esterification.

The synthesis of 1-octene starting from butadiene is known in the state of the art.

Some patents describe the synthesis of 1-octene from butadiene by means of a three-step process. In U.S. Pat. No. 5,030,792, in a first step the catalytic telomerization of butadiene is effected with acetic acid to give 2,7-octadienyl acetate; the latter, in a second step, is hydrogenated to n-octyl acetate which, in turn, in a third step, is pyrolyzed to 1-octene. This type of process is jeopardized by the high number of reaction steps and is also characterized by corrosion problems of the common materials linked to the use of acetic acid.

WO 92/10450 describes the catalytic telomerization of butadiene with an alcohol such as methanol or ethanol to give 2,7-octadienyl ether. The latter, in a second step, is hydrogenated to octyl ether which, in turn, in a third step, is pyrolyzed to 1-octene. Although it avoids the use of corrosive carboxylic acids, this type of process is also jeopardized by the high number of reaction steps and an overall lower selectivity.

Finally, WO 03/31378 describes the synthesis of 1-octene in only two steps starting from butadiene according to the scheme of equations (1) and (2)

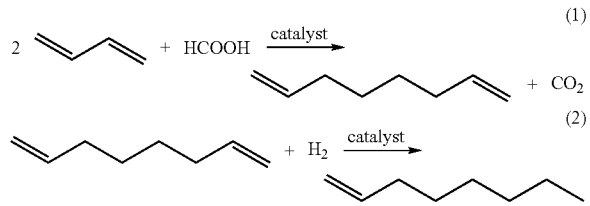

In the first step of the process described, the catalytic bis-hydrodimerization of butadiene to 1,7-octadiene is effected with a reducing agent such as formic acid. In the second step, the partial catalytic hydrogenation is carried out, of 1,7-octadiene to 1-octene.

Although the process described in WO 03/31378 has the advantage, with respect to the previous processes, of reducing the number of steps necessary for producing 1-octene from butadiene, to two, it has numerous drawbacks and in particular the necessity of using, both in the first and in the second step, high quantities of costly noble metals as catalysts.

The first step of the process of WO 03/31378 is carried out according to a reaction known in literature, i.e. the bis-hydrodimerization of butadiene in the presence of formic acid and catalysts based on palladium and phosphines. The reaction described is, in all cases, scarcely selective, with the formation of mixtures of 1,6-octadiene and 1,7-octadiene; and the yields and catalytic efficiency, moreover, are low.

Furthermore, it is necessary to use high quantities of catalyst, which create problems relating to the cost and recovery of the catalyst itself. If the concentration of catalyst is reduced to lower values, the selectivity to 1,7-octadiene decreases.

From what is specified above, it would appear necessary to avail of a more efficient process for the hydrodimerization of butadiene which allows high conversions and selectivities to 1,7-octadiene to be reached, also when operating with reduced concentrations of noble metal.

The second step of the process described in WO 03/31378 consists in the partial hydrogenation of 1,7-octadiene to 1-octene. The reaction, as described in WO 03/31378, i.e. carried out with a supported catalyst based on ruthenium in heterogeneous phase, suffers from an extremely low catalytic activity. Very long reaction times, in the order of over 24 hours, are in fact required for obtaining a conversion of 1,7-octadiene of 70% and a selectivity to 1-octene of 60%, and furthermore, it does not avoid the formation of isomer olefins. Also in this case, the quantity of catalyst used (i.e. supported ruthenium) is much higher, due to the low catalytic activity of the catalyst adopted.

The necessity is therefore felt, also for this step, for a more efficient and more selective partial reduction of the 1,7-octadiene, even when operating with low quantities of catalyst.

A process has now been found for the preparation of 1-octene starting from butadiene, which overcomes the above drawbacks.

In accordance with this, the present invention relates to a process in two steps for the preparation of 1-octene starting from butadiene which comprises:

a first step (a) in which the bis-hydrodimerization of butadiene to 1,7-octadiene is effected in the presence of a catalyst based on a palladium complex containing one or more tri-substituted monodentate phosphines, in an aprotic polar solvent, optionally containing an organic base; the above first step being carried out in the presence of a hydrogen donor, preferably formic acid;

a second step (b) in which the partial catalytic hydrogenation of 1,7-octadiene, recovered at the end of the first step, to 1-octene, is effected; the above hydrogenation being carried out in an inert solvent, under hydrogen pressure or mixtures of hydrogen and nitrogen, in the presence of a catalyst;

the above process being characterized in that:
(i) in the first step the aprotic polar solvent is selected from disubstituted cyclic ureas having general formula (I)

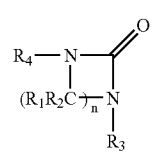

wherein n ranges from 1 to 8, preferably from 2 to 3;
$R_1$ and $R_2$, the same or different, are selected from H and a $C_1$-$C_6$ alkyl radical, preferably $R_1$=$R_2$=H;
$R_3$ and $R_4$, the same or different, are selected from $C_1$-$C_{16}$, preferably $C_1$-$C_3$, alkyl radicals (ii) in the second step the catalyst is selected from non-supported ruthenium complexes having general formula (II):

$$RuX_mL_n \qquad (II),$$

wherein:

X is selected from Cl, Br, I, CH$_3$COO, H, =C(H)Ph;

L is selected from monodentate or bidentate neutral ligands;

n ranges from 2 to 4;

m ranges from 1 to 3.

Typical examples of disubstituted cyclic ureas having general formula (I) are dimethyl ethylene urea (n=2; R$_1$=R$_2$=H; R$_3$=R$_4$=CH$_3$) and dimethyl propylene urea (n=3; R$_1$=R$_2$=H; R$_3$=R4=CH$_3$).

Using the particular solvents of the present invention in the first step, i.e. disubstituted cyclic ureas, it is possible, with all the other conditions remaining unaltered, to increase the conversion of butadiene and selectivity to 1,7-octadiene. This means that it is possible to decrease the quantity of catalyst used to extremely reduced concentrations, without reducing the conversion of butadiene and selectivity of 1,7-octadiene, which are maintained high.

Again with respect to the first step (a), i.e. the bis-hydrodimerization of butadiene to 1,7-octadiene, the palladium-based catalyst can be preformed or formed in situ. In the latter case, the catalyst is formed in situ starting from a palladium salt and one or more phosphines. In the preferred embodiment, the palladium salt is selected from palladium carboxylates, even more preferably from Pd(Me$_3$CCOO)$_2$ and Pd(acetate)$_2$. As far as the phosphine is concerned, typical examples are triphenyl phosphine, tri(o-tolyl)phosphine, (3-sulfonatephenyl) diphenyl phosphine, tricyclohexyl phosphine, trimethyl phosphine, triethyl phosphine, triisopropyl phosphine, tributyl phosphine, and mixed phosphines methyl diphenyl phosphine, dimethyl phenyl phosphine, singly or combined with each other. Triphenyl phosphine is preferred. In the case of the formation in situ of the palladium complex, the molar ratio between the phosphines and palladium ranges from 1 to 100, preferably from 2 to 40.

In the preferred embodiment, the palladium is preformed and consists of one or more palladium complexes having the general formula PdX$_2$(PR$_3$)$_2$, wherein X=Cl, Br, acetate, and R$_3$ is a C$_1$-C$_{16}$ hydrocarbyl radical, preferably selected from phenyl, o-tolyl, methyl, tricylcohexyl, ethyl, isopropyl, butyl and relative mixtures. The following complexes are preferred: PdCl$_2$(PEt$_3$)$_2$, PdCl$_2$(PCy$_3$)$_2$, PdCl$_2$(PBut$_3$)$_2$, PdCl$_2$(PiPr$_3$)$_2$, wherein Et=ethyl, Cy=cyclohexyl, iPr=isopropyl, But=n-butyl.

As far as the organic base which can be optionally used in the first step, is concerned, typical examples are pyridines, N-alkyl morpholines, trialkyl amines. In the preferred embodiment, the organic base is triethyl amine.

The first step is carried out in the presence of a hydrogen donor, preferably in a stoichiometric ratio of 1:2 molar with respect to the butadiene, see equation (1), or slightly lower. The hydrogen donor is preferably formic acid.

The butadiene is used in an initial weight ratio ranging from 1:10 to 10:1 with respect to the solvent, more preferably from 1:5 to 5:1.

The hydrogen donor, preferably formic acid, is used, in a preferred embodiment, in a stoichiometric ratio (i.e. 1/2 molar) with respect to the butadiene, or slightly lower than the stoichiometric value.

The molar ratio between the organic base, for example triethyl amine and the hydrogen donor, for example formic acid, can vary from 0 to 1.5, more preferably from 0.2 to 1.3, and even more preferably from 0.4 to 0.8.

Step (a) is carried out at temperatures ranging from 50 to 120° C., preferably from 70 to 100° C., preferably under a nitrogen pressure ranging from 0.5-2 MPa, more preferably from 0.8 to 1.5 MPa.

The duration of the reaction of step (a) indicatively ranges from 10 to 180 minutes, more preferably from 15 to 120 minutes.

According to the above process, in the first step, it is possible to improve the selectivity to 1,7-octadiene even in the presence of extremely reduced quantities of catalyst, for example such that the initial molar ratio butadiene/palladium ranges from 5,000 to 1,000,000, preferably from 20,000 to 200,000, without significantly jeopardizing the conversion of the butadiene, which is maintained high.

At the end of the first step, the reaction product 1,7-octadiene can be recovered according to the conventional techniques. More specifically, in a preferred embodiment of the invention, the reaction product is separated by demixing, exploiting the fact that 1,7-octadiene is not miscible in all ratios with disubstituted cyclic ureas.

The upper hydrocarbon phase, prevalently consisting of 1,7-octadiene, can be purified from the non-hydrocarbon residues by washing with water; the 1,7-octadiene is subsequently purified with conventional methods, for example by distillation.

The second step of the process, i.e. the partial catalytic hydrogenation of 1,7-octadiene to 1-octene, is carried out in the presence of a catalyst consisting of a ruthenium complex. The catalyst is preferably selected from ruthenium complexes having the formula RuX$_m$L$_n$, wherein: m ranges from 1 to 3, n ranges from 2 to 4; X=Cl, Br, I, CH$_3$COO, H, =C(H)Ph; L=a monodentate neutral ligand such as: PPh$_3$ (Triphenyl phosphine), PCy$_3$ (Tricyclohexyl phosphine), P(o-CH$_3$C$_6$H$_4$)$_3$ (triortho-tolyl phosphine), CO (carbon monoxide); or L=a bidentate neutral ligand such as: diphenyl phosphine ethane (dppe), dipyridyl (bipy), 1,10-phenanthroline (Phen), 4.7-diphenyl-1,10 -phenanthroline (bato), used alone or also combined with each other.

More specifically, the following ruthenium complexes are preferred: RuCl$_2$(PPh$_3$)$_3$, RuCl$_2$(PPh$_3$)$_4$, RuCl$_2$(CO)(PPh$_3$)$_3$, RuHCl(PPh$_3$)$_3$, RuHCl(CO)(PPh$_3$)$_3$, RuCl$_2$(dppe)$_2$, RUCl$_2$(PCy$_3$)$_3$, RUCl$_2$(CO)$_2$(PPh$_3$)$_2$, (PCy$_3$)$_2$Cl$_2$Ru=C(H)Ph, [Ru(CO)$_2$Cl$_2$]$_x$. Among the most preferred catalysts, RuCl$_2$(PPh$_3$)$_x$ with x=3 or 4, is used.

The ruthenium complex is added to the reaction mixture in a molar ratio, with respect to 1,7-octadiene, ranging from 1/100 to 1/500,000, preferably from 1/1,000 to 1/150,000, even more preferably from 1/5,000 to 1/50,000.

Step (b) can be carried out in a solvent or in the pure diene, preferably in the presence of a solvent. Suitable solvents are alcohols having the general formula R—OH, wherein R is an alkyl radical containing from 1 to 6 carbon atoms; ethers R—O—R', wherein R and R' have the meaning described above for R; cyclic ethers containing up to 6 carbon atoms, linear or branched aliphatic hydrocarbons containing from 5 to 16 carbon atoms; partially or totally halogenated hydrocarbons containing from 1 to 3 carbon atoms, aromatic or alkyl aromatic hydrocarbons containing up to 9 carbon atoms; ketones containing up to 6 carbon atoms. The solvents are preferably selected from methanol, ethanol, propanol and mixtures thereof.

Mixtures of solvents non entirely miscible with each other can also be used as solvents, such as methanol and C$_8$-C$_{16}$ aliphatic hydrocarbons. The use of these mixtures of solvents simplifies the separation of the catalyst from the reaction mixture due to the greater affinity of the catalyst for the alcohol phase. In an even more preferred embodiment, the second step is carried out in a methanol solution, and 1-octene (together with the possible nonreacted 1,7-octadiene and possible octane co-produced) can be extracted from the reaction mixture with a $C_8$-$C_{16}$ aliphatic hydrocarbon, preferably dodecane, by means of liquid-liquid extraction according to the conventional techniques, leaving the catalyst, which can be recycled to the reaction, in the methanol solution. 1-octene is then recovered from the hydrocarbon mixture, and purified with conventional methods.

When a solvent is used, the diene is contained in the solvent in a ratio ranging from 5 to 90% by weight, more preferably from 10 to 80% by weight.

The reaction of step (b) is generally carried out at a temperature ranging from 0° C. to 150° C., preferably from 5° C. to 60° C. This range represents the temperature field in which the catalytic system has the minimum isomerization activity of the double bond compatible with a good hydrogenation rate.

The reaction is generally carried out under a hydrogen pressure or mixtures of hydrogen and nitrogen, preferably in the presence of hydrogen alone, at a pressure ranging from 0.05 to 10 MPa, preferably from 0.1 to 3 MPa.

The reaction time indicatively ranges from 2 to 200 minutes, more preferably from 5 to 60 minutes.

In order to limit the consecutive hydrogenation reaction of 1-octene to octane, the reaction is preferably carried out at a partial conversion of 1,7-octadiene lower than 80%, preferably ranging from 40 to 60%.

When the conversion value is within this range, selectivities to 1-octene generally ranging from 75 to 90%, are obtained. Furthermore, when operating according to the invention, the other isomers of 1-octene and 1,7-octadiene are normally absent.

The following examples are provided for a better understanding of the present invention.

EXAMPLES

Synthesis of 1,7-octadiene

Examples 1 to 14

Catalyst Formed in Situ

The following products are placed, in the order indicated and in the type and quantities specified in Table 1 or hereunder, in a Hastelloy C autoclave having a volume of 300 ml and equipped with a mechanical stirring system and heating system: the solvent, the organic base (if present), 7 ml of formic acid (concentration 99% by weight) in a stoichiometric quantity with respect to the butadiene, triphenyl phosphine as ligand and $Pd(CH_3COO)_2$ as catalyst. Finally, the autoclave is closed and 20 g of butadiene are added. The autoclave is pressurized with nitrogen at 1.0 MPa and the heating is initiated to a temperature of 90° C. for the time indicated in Table 1. At the end, the autoclave is cooled, the contents are treated with water and sodium bicarbonate and are extracted with cyclohexane. The products are quantified by gas chromatography with the internal standard method. The conversion of butadiene and selectivities referring to the butadiene converted are indicated in Table 21.

TABLE 1

|  | Mol. Ratio $PPh_3$/Pd | Solvent ml | $NEt_3$ Ml | Time min | Mol. ratio BD/Pd | Conv. % BD | Sel. % 1,6-oct. | Sel % 1,7-oct. |
|---|---|---|---|---|---|---|---|---|
| Ex. 1 comp. | 2 | DMF 45 | 15 | 90 | 1829 | 65 | 22 | 76 |
| Ex. 2 comp. | 2 | DMA 45 | 15 | 180 | 1627 | 24 | 74 | 21 |
| Example 3 | 2 | DMPU 45 | 15 | 60 | 1813 | 78 | 13 | 84 |
| Ex. 4 comp. | 21 | DMF 60 | 0 | 120 | 5475 | 63 | 10 | 88 |
| Ex. 5 comp. | 20 | NMP 60 | 0 | 60 | 6326 | 49 | 93 | 6 |
| Ex. 6 comp. | 19 | TMU 60 | 0 | 60 | 5922 | 2 | 12 | 83 |
| Ex. 7 comp. | 19 | THF 60 | 0 | 120 | 4208 | 64 | 15 | 77 |
| Example 8 | 20 | DMPU 60 | 0 | 120 | 5759 | 71 | 9 | 90 |
| Ex. 9 comp. | 19 | DMF 45 | 15 | 120 | 4863 | 60 | 9 | 88 |
| Example 10 | 22 | DMPU 45 | 15 | 120 | 5415 | 78 | 9 | 89 |
| Ex. 11 comp. | 21 | DMF 45 | 15 | 90 | 23526 | 61 | 10 | 89 |
| Example 12 | 20 | DMEU 45 | 15 | 90 | 24449 | 67 | 9 | 90 |
| Ex. 13 comp. | 20 | DMF 45 | 15 | 90 | 53972 | 42 | 10 | 89 |
| Example 14 | 20 | DMEU 15 | 15 | 90 | 48355 | 58 | 9 | 90 |

NMP = N-methyl pyrrolidone; THF = tetrahydrofuran; TMU = tetramethyl urea; DMEU = dimethyl ethylene urea; DMPU = di-methyl propylene urea.

Table 1 clearly shows how, when operating with cyclic ureas as solvent, the other conditions remaining unaltered, the conversion of butadiene increases, whereas the selectivity to 1,7-octadiene remains the same or improves.

Examples 15 to 20

Preformed Catalyst

The following products are placed, in the order indicated and in the type and quantities specified in Table 2 or hereunder, in a Hastelloy C autoclave having a volume of 300 ml and equipped with a mechanical stirring system and heating system: 45 ml of solvent, 15 ml of triethyl amine, 7 ml of formic acid (concentration 99% by weight) in a stoichiometric quantity with respect to the butadiene, and the catalyst in the molar ratio with respect to the butadiene specified in Table 2. Finally, the autoclave is closed and 20 g of butadiene are added. The autoclave is pressurized with nitrogen at 1 MPa and the heating is initiated to a temperature of 90° C. for 120 minutes. At the end, the autoclave is cooled, the contents are treated with water and sodium bicarbonate and are extracted with cyclohexane. The products are quantified by gas chromatography with the internal standard method. The conversion of butadiene and selectivities referring to the butadiene converted are indicated in Table 2.

TABLE 2

|  | Catalyst | Solvent[a] | Mol. ratio BD/Pd | Conv. % BD | Sel. % 1,6-octad. | Sel. % 1,7-octad. |
|---|---|---|---|---|---|---|
| Comp. ex. 15 | $PdCl_2(PBu_3)_2$ | DMF | 104405 | 38 | 6 | 94 |
| Example 16 | $PdCl_2(PBu_3)_2$ | DMEU | 105871 | 49 | 3 | 97 |
| Comp. ex. 17 | $PdCl_2(PEt_3)_2$ | DMF | 104138 | 35 | 7 | 93 |
| Example 18 | $PdCl_2(PEt_3)_2$ | DMEU | 104383 | 38 | 5 | 95 |
| Comp. ex. 19 | $PdCl_2(PCy_3)_2$ | DMF | 101215 | 18 | 6 | 94 |
| Example 20 | $PdCl_2(PCy_3)_2$ | DMEU | 119159 | 34 | 4 | 96 |

$PBu_3$ = Tri-n-butyl phosphine; $PET_3$ = Triethyl phosphine; $PCy_3$ = Tricyclohexyl phosphine.

Table 2 clearly shows that, when operating with cyclic ureas as solvent and using preformed palladium catalysts, with the other conditions remaining unaltered, there is an increase in both the conversion of butadiene and also, to a lesser extent, the selectivity to 1,7-octadiene.

Hydrogenation of 1,7-octadiene to 1-octene

Examples 21 to 25

100 ml of methanol, the quantity of 1,7-octadiene (1,7-OD) which is such as to reach the desired 1,7-OD/catalyst ratio, as indicated in Table 3 and 0.01 mmoles of catalyst are place in order into a 250 ml glass flask put under Argon. The solution is well mixed until the complete dissolution of the catalyst and is then transferred by means of a steel needle, exploiting the difference in pressure, to a Hastelloy c autoclave having a volume of 300 ml, equipped with a mechanical stirring and heating system, previously brought under vacuum. The Argon pressure in the autoclave is brought to a level slightly higher than atmospheric value. The autoclave is heated (or cooled) to the desired temperature and hydrogen is then introduced by pressurizing the autoclave at a pressure of 2 MPa and connecting it to a make-up system of the used-up hydrogen. The reaction is thus initiated. A sample is taken from the autoclave at pre-established times and is analyzed by gas chromatography with the internal standard method to determine the residual 1,7-octadiene of the 1-octene and 1-octane products and for the diene and monoene isomers. The selectivities refer to the 1,7-octadiene converted. The results obtained are indicated in Table 3.

TABLE 3

|  | Catalyst | Molar ratio OD/Cat. | T °C. | t min. | Conv. % 1,7-OD | Select. % 1-octene | Select. % octane | Select. % isomers |
|---|---|---|---|---|---|---|---|---|
| Ex. 21 | $RuCl_2(PPh_3)_4$ | 18789 | 55 | 2 | 32% | 90% | 9% | 0% |
|  |  |  | 52 | 5 | 37% | 88% | 11% | 0% |
|  |  |  | 50 | 10 | 48% | 82% | 17% | 0% |
|  |  |  | 50 | 20 | 91% | 62% | 38% | 0% |
| Ex. 22 | $RuCl_2(PPh_3)_4$ | 19683 | 8 | 5 | 9% | 96% | 4% | 0% |
|  |  |  | 11 | 10 | 45% | 83% | 17% | 0% |
|  |  |  | 14 | 15 | 88% | 52% | 48% | 0% |
|  |  |  | 8 | 25 | 98% | 27% | 73% | 0% |
| Ex. 23 | $RuCl_2(PPh_3)_4$ | 41335 | 8 | 5 | 14% | 95% | 5% | 0% |
|  |  |  | 8 | 10 | 23% | 93% | 7% | 0% |
|  |  |  | 7 | 20 | 38% | 88% | 12% | 0% |
|  |  |  | 7 | 40 | 62% | 78% | 22% | 0% |
|  |  |  | 5 | 80 | 81% | 62% | 38% | 0% |
| Ex. 24 | $RuCl_2(PPh_3)_4$ (a) | 9254 | 25 | 5 | 39% | 84% | 16% | 0% |
|  |  |  | 24 | 15 | 65% | 76% | 24% | 0% |
|  |  |  | 23 | 35 | 70% | 69% | 31% | 0% |
|  |  |  | 23 | 95 | 84% | 60% | 39% | 0% |
| Ex. 25 | $RuCl_2(=C(H)C_8H_5)(PCy_3)_2$ | 19934 | 31 | 5 | 9% | 94% | 6% | 0% |
|  |  |  | 30 | 15 | 11% | 93% | 8% | 0% |
|  |  |  | 30 | 45 | 24% | 89% | 11% | 0% |
|  |  |  | 30 | 75 | 30% | 86% | 14% | 1% |

(a) effected in a solution of methanol/dodecane 1/1 by volume

Table 3 shows how, when operating according to the invention, in a solution of methanol, the hydrogenation reaction of 1,7-octadiene to 1-octene takes place in a few minutes, in relation to the concentration of catalyst, in the absence of the isomerization of 1,7-octadiene and 1-octene.

The invention claimed is:

1. A process in two steps for the preparation of 1-octene starting from butadiene which comprises:
   a first step (a) in which the bis-hydrodimerization of butadiene to 1,7-octadiene is effected in the presence of a catalyst based on a palladium complex containing one or more tri-substituted monodentate phosphines, in an aprotic polar solvent optionally containing an organic base; the above first step being carried out in the presence of a hydrogen donor;
   a second step (b) in which the partial catalytic hydrogenation of 1,7-octadiene, recovered at the end of the first step, to 1-octene, is effected; the above hydrogenation being carried out in an inert solvent, under hydrogen pressure or mixtures of hydrogen and nitrogen, in the presence of a catalyst;
   the above process being characterized in that:
   (i) in the first step the aprotic polar solvent is selected from disubstituted cyclic ureas having general formula (I)

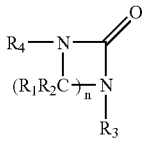

wherein n ranges from 1 to 8;
$R_1$ and $R_2$, the same or different, are selected from H and a $C_1$-$C_6$ alkyl radical;
$R_3$ and $R_4$, the same or different, are selected from $C_1$-$C_{16}$ alkyl radicals;
(ii) in the second step the catalyst is selected from non-supported ruthenium complexes having general formula (II):

$$RuX_mL_n \quad (II)$$

wherein:
X is selected from Cl, Br, I, $CH_3COO$, H, $=$C(H)Ph;
L is selected from monodentate or bidentate neutral ligands;
m ranges from 1 to 3;
n ranges from 2 to 4.

2. The process according to claim 1, wherein in the compound having general formula (I), n is between 2 and 3; $R_1$=$R_2$=H; $R_3$=$R_4$=$CH_3$.

3. The process according to claim 1, wherein the palladium complex in step (a) is a preformed complex having the general formula $PdX_2(PR_3)_2$ wherein X=Cl, Br, acetate, and $R_3$ is a $C_1$-$C_{16}$ hydrocarbyl radical.

4. The process according to claim 1, wherein the organic base used in step 1 is triethyl amine.

5. The process according to claim 1, wherein the butadiene is used in an initial weight ratio with respect to the solvent ranging from 1:10 to 10:1.

6. The process according to claim 5, wherein the butadiene is used in a weight ratio with respect to the solvent ranging from 1:5 to 5:1.

7. The process according to claim 1, wherein the hydrogen donor is in a stoichiometric ratio of 1:2 molar with respect to the butadiene.

8. The process according to claim 1, wherein the hydrogen donor is formic acid.

9. The process according to claim 1, wherein the molar ratio between the organic base and hydrogen donor ranges from 0 to 1.5.

10. The process according to claim 1, wherein step (a) is carried out at temperatures ranging from 50 to 120° C.

11. The process according to claim 1, wherein in the complex $Rux_mL_n$, m ranges from 2 to 3; n ranges from 2 to 4; X is selected from the group consisting of Cl and $=$CHPh; L is a phosphine.

12. The process according to claim 11, wherein X=Cl, m=2, n=4, L =$PPh_3$.

13. The process according to claim 11, wherein m=3 n=2 L=$PCy_3$.

14. The process according to claim 1, wherein the ruthenium complex in step (b) is present in the reaction mixture in a molar ratio with respect to 1,7-octadiene, ranging from 1/100 to 1/500,000, more preferably from 1/5,000 to 1/50,000.

15. The process according to claim 1, wherein 1,7-octadiene is contained in the solvent in a ratio ranging from 5 to 90% by weight.

16. The process according to claim 1, wherein step (b) is carried out at a temperature ranging from 0° C. to 150° C.

17. The process according to claim 1, wherein step (b) is carried out in the presence of mixtures of hydrogen and nitrogen, or in the presence of hydrogen alone, at a pressure ranging from 0.05 to 10 MPa.

* * * * *